(12) United States Patent
Stewart

(10) Patent No.: US 6,544,255 B2
(45) Date of Patent: Apr. 8, 2003

(54) METHOD OF HAIR REMOVAL BY TRANSCUTANEOUS APPLICATION OF LASER LIGHT

(75) Inventor: Bob W. Stewart, Cincinnati, OH (US)

(73) Assignee: Keralase Ltd., Calgary (CA)

( * ) Notice: Subject to any disclaimer, the term of this patent is extended or adjusted under 35 U.S.C. 154(b) by 0 days.

(21) Appl. No.: 09/811,177

(22) Filed: Mar. 15, 2001

(65) Prior Publication Data

US 2002/0022828 A1 Feb. 21, 2002

Related U.S. Application Data

(63) Continuation of application No. 09/225,398, filed on Jan. 6, 1999, now Pat. No. 6,248,102, which is a continuation-in-part of application No. 08/832,920, filed on Apr. 4, 1997, now abandoned.

(51) Int. Cl.[7] ................................................ A61B 18/18
(52) U.S. Cl. ............................................ 606/9; 606/13
(58) Field of Search ............................... 606/9, 13, 16, 606/17; 607/89

(56) References Cited

U.S. PATENT DOCUMENTS

| | | |
|---|---|---|
| 3,538,919 A | 11/1970 | Meyer |
| 4,385,798 A | 5/1983 | Yevick |
| 4,388,924 A | 6/1983 | Weissman et al. |
| 4,617,926 A | 10/1986 | Sutton |
| 5,059,192 A | 10/1991 | Zaias |
| 5,226,907 A | 7/1993 | Tankovich |
| 5,304,170 A | 4/1994 | Green |
| 5,317,148 A | 5/1994 | Gray et al. |
| 5,403,306 A | 4/1995 | Edwards et al. |
| 5,464,436 A | 11/1995 | Smith |
| 5,505,727 A | 4/1996 | Keller |
| 5,595,568 A | 1/1997 | Anderson et al. |
| 5,630,811 A | 5/1997 | Miller |
| 5,632,741 A | 5/1997 | Zavislan et al. |
| 5,647,866 A | 7/1997 | Zaias et al. |
| 5,655,547 A | 8/1997 | Karni |
| 5,715,337 A | 2/1998 | Spitzer et al. |
| 5,735,844 A | 4/1998 | Anderson et al. |
| 5,817,089 A | 10/1998 | Tankovich et al. |
| 5,853,407 A | 12/1998 | Miller |
| 5,860,967 A * | 1/1999 | Zavislan et al. ............. 606/10 |

FOREIGN PATENT DOCUMENTS

| | | |
|---|---|---|
| CA | 850256 | 8/1970 |
| CA | 1210458 | 8/1986 |
| CA | 2178631 | 6/1995 |
| CA | 2131750 | 1/1996 |
| CA | 2210720 | 8/1996 |
| CA | 2240842 | 6/1997 |
| CA | 2222222 | 10/1997 |
| CA | 2024271 | 12/1997 |
| CA | 2294983 | 1/1999 |
| EP | 0601130 B1 | 8/1998 |
| GB | 2308307 A | 12/1996 |
| WO | PCT/US83/00068 | 1/1983 |
| WO | PCT/GB94/02682 | 12/1994 |
| WO | PCT/US96/01235 | 1/1996 |
| WO | PCT/GB97/00354 | 2/1997 |
| WO | PCT/US97/05560 | 4/1997 |
| WO | PCT/US99/06475 | 3/1999 |

OTHER PUBLICATIONS

U.S. Provisional Patent Application No. 60/079,710, filed Mar. 27, 1998, entitled Method and Apparatus for the Ablation of Lipid–Rich Tissues, relied upon for a claim of priority in PCT International Application No. PCT/US99/06475.

* cited by examiner

Primary Examiner—Roy D. Gibson
(74) Attorney, Agent, or Firm—Christensen O'Connor Johnson Kindness PLLC

(57) ABSTRACT

A method of hair removal, used primarily for cosmetic purposes, comprising the transcutaneous use of laser light having a wavelength which targets the keratin components of hair, thus destroying the hair by photothermolysis without damage to surrounding skin or tissue; this primary method may be supplemented by the use of intrafollicular hair removal methods utilizing a second wavelength of light produced by the same source used to generate the primary light wavelength.

6 Claims, 3 Drawing Sheets

METHOD OF HAIR REMOVAL BY TRANSCUTANEOUS APPLICATION OF LASER LIGHT

CROSS-REFERENCE TO RELATED APPLICATION

This is a continuation of U.S. application Ser. No. 09/225,398 filed Jan. 6, 1999 now U.S. Pat. No. 6,248,102, which is a continuation-in-part of U.S. application Ser. No. 08/832,920 filed Apr. 4, 1997 now abandoned.

BACKGROUND OF THE INVENTION

1. Field of the Invention

The invention relates generally to a method of permanent hair removal using laser light. More specifically, the invention relates to the transcutaneous use of laser light to target the keratin component of hair, thus destroying the hair by photothermolysis without damage to surrounding skin or tissue.

2. Description of the Prior Art

Currently available laser hair removal methods may be classified as either intrafollicular or transcutaneous in nature. Intrafollicular methods comprise the delivery of laser light through a small probe tip to the hair follicle. The light utilized is of a wavelength which is readily absorbed by either the melanin in the hair or the hemoglobin in the blood vessels surrounding the papilla. This absorption of light energy produces heat, resulting in damage to the hair shaft, photocoagulation of the tissue surrounding the papilla, and subsequent destruction of the hair. Because the light energy employed in this method is absorbed by either blood or melanin in the skin, it requires the use of a very narrow beam of light to target a single hair at a time and prevent damage to the surrounding tissue. This results in a painstaking, time-consuming process which must be administered by a skilled operator. When targeting melanin, this method losses effectiveness when used on lighter haired or darker skinned patients. In addition, some methods in this category require that the needle-like probe tip be inserted into the hair follicle, a painful process which must be repeated for every hair.

Transcutaneous laser hair removal methods currently available utilizes a substance which is massaged into the skin to penetrate the hair ducts. After cleaning the substance from the skin's surface, light of a wavelength which passes through the skin, but which is absorbed by the substance, is directed onto the treated area. The absorption of energy by the substance applied to the hair duct causes photocoagulation of the tissue surrounding the papilla and results in destruction of the hair. Although this method allows for treatment of a sizeable area of skin, it requires the inconvenient, time consuming application of the light-absorbing substance. In addition, great care must be taken to completely remove the substance from the skin's surface prior to the laser treatment to avoid damage to the skin.

Because of the disadvantages associated with both methods of hair removal in use today, a new method is needed which provides faster, more convenient, and less painful permanent hair removal without damage to the patient's skin.

SUMMARY OF THE INVENTION

The invention relates to a method of permanent hair removal used primarily for cosmetic purposes. This method comprises the transcutaneous use of laser light having wavelength in the 900–950 nanometer range wherein the light is directed onto an area of skin on which hair removal is desired. Light of this wavelength passes through the skin with only minimal absorption by blood, blood components, and melanin. This wavelength is, however, readily absorbed by the protein keratin, the main component of hair of all colors. Absorption of the light energy by the keratin produces heat, which damages the hair shaft and root and photocoagulates the blood vessels and tissue surrounding the papilla, resulting in destruction of the hair and preventing its re-growth.

In its preferred embodiment, the method also includes the use of a second wavelength of laser light produced by known means, such as second harmonic generation or 3-mixing plus second harmonic generation, from the same laser source which generates the primary 900–950 nm wavelength. This second wavelength of light, which will be in the 450–475 nanometer range, is readily absorbed by both blood components and melanin. An intrafollicular probe is used to deliver the second wavelength of light to the hair follicle, in the manner described in the prior art, to treat the small percentage of hairs having papillae at a skin depth beyond the effective range of the primary wavelength of light. In this fashion, a single laser light source can be used to treat all types of hair in the least painful and most efficient, cost effective, and convenient manner possible.

There are numerous problems associated with the hair removal methods in the field of prior art. Some of these methods are painful for the patient. Others have varying effectiveness depending on the skin and hair color of the patient. Most must be administered by highly skilled operators to reduce the risk to the patient. All of these methods involve expensive, painstaking, and time-consuming processes. In addition, all carry substantial risk of skin damage if not performed properly.

It is an object of the invention to provide a hair removal method which: 1) is fast and convenient; 2) is less painful; 3) is effective on hair of all types; 4) has reduced risk for skin damage; and 5) utilizes a low cost, low maintenance, and low power consumption laser source. Further objects and advantages of the invention will become apparent from a consideration of the drawings and description.

Figure 1:
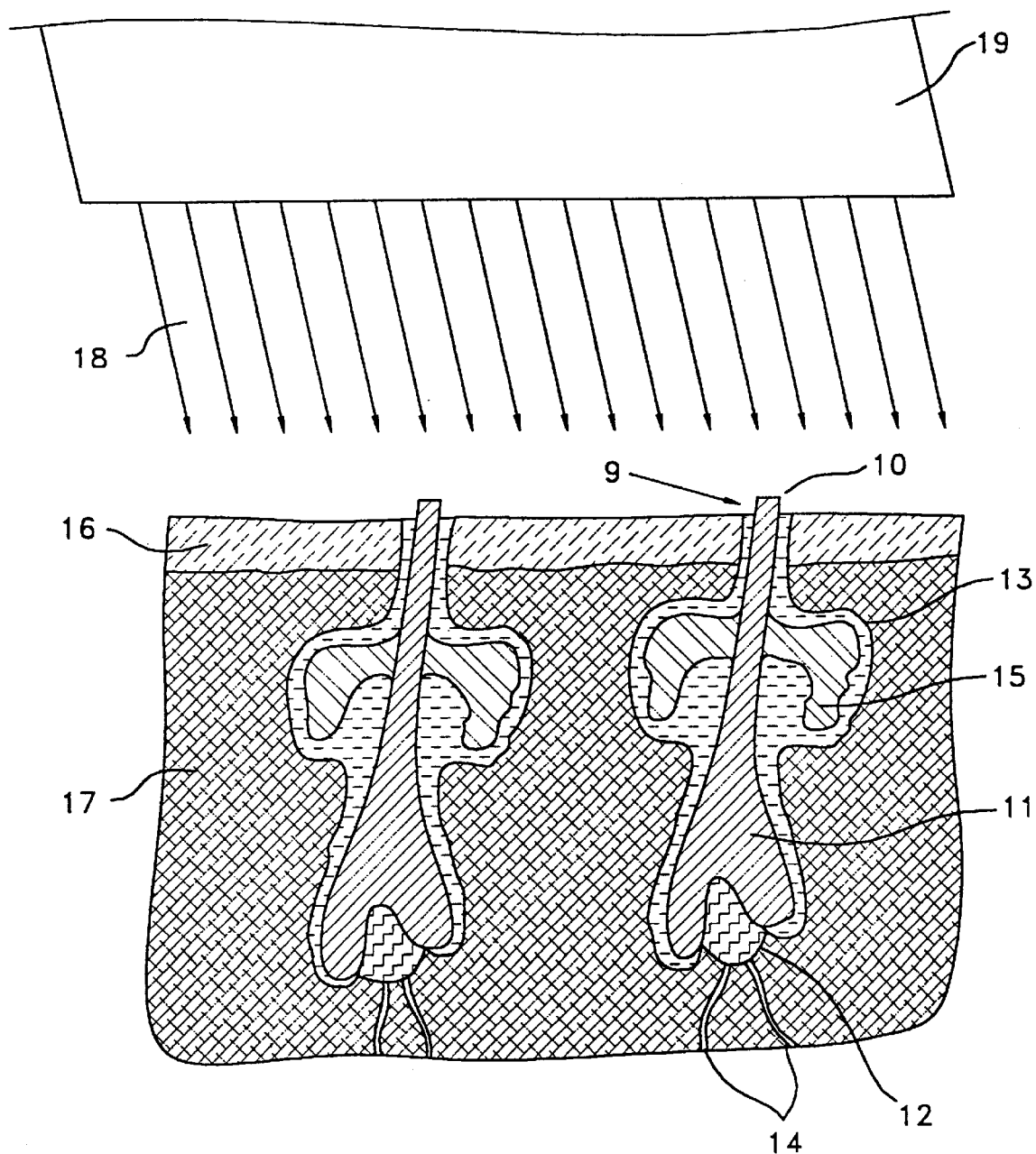
FIG. 1 is a sectional view of an area of skin showing the structure of hair and skin and the transcutaneous application of laser light.

DRAWING REFERENCE NUMERALS 9 hair
10 shaft
11 root
12 papilla
13 follicle
14 blood vessels
15 sebaceous glands
16 epidermis
17 dermis
18 laserlight
19 fiber optic cable probe tip
20 intrafollicular probe

DESCRIPTION OF THE PREFERRED EMBODIMENT

Description:

FIG. 1 illustrates the preferred embodiment of the invention. As shown, laser light 18 emanates from the probe tip 19 of a fiber optic cable, not shown, and is directed onto the surface of the skin. The optical elements of the probe are not in contact with the surface of the skin, in the transcutaneous approach. Non-contact avoids the contamination of the optical components by surface substances, such as sebum, and therefore reduces the need for post-treatment cleansing of the optics, a process which can remove the anti-reflective coatings on them, thereby reducing the amount of energy reaching the skin's surface and making accurate dosage difficult. The other end of the fiber optic cable is connected to a laser light source, also not shown. The size and shape of the light beam may be customized to meet the requirements of any individual application. FIG. 1 also illustrates the structure of hairs 9 and the surrounding upper and lower skin layers, known as the sepidermis 16 and the dermis 17, respectively. Hair 9 comprises shaft 10, shown shaved near the surface of the skin, and root 11. Follicle 13 is a sac which encloses shaft 10, root 11, and adjacent sebaceous glands 15. Located at the lower end of follicle 13 is the papilla 12, which is fed by blood vessels 14 and provides nourishment to root 11. In order to prevent regrowth of hair 9, it is the papilla 12 and blood vessels 14 which must be damaged sufficiently to prevent continued nourishment of root 11.

Figure 2:
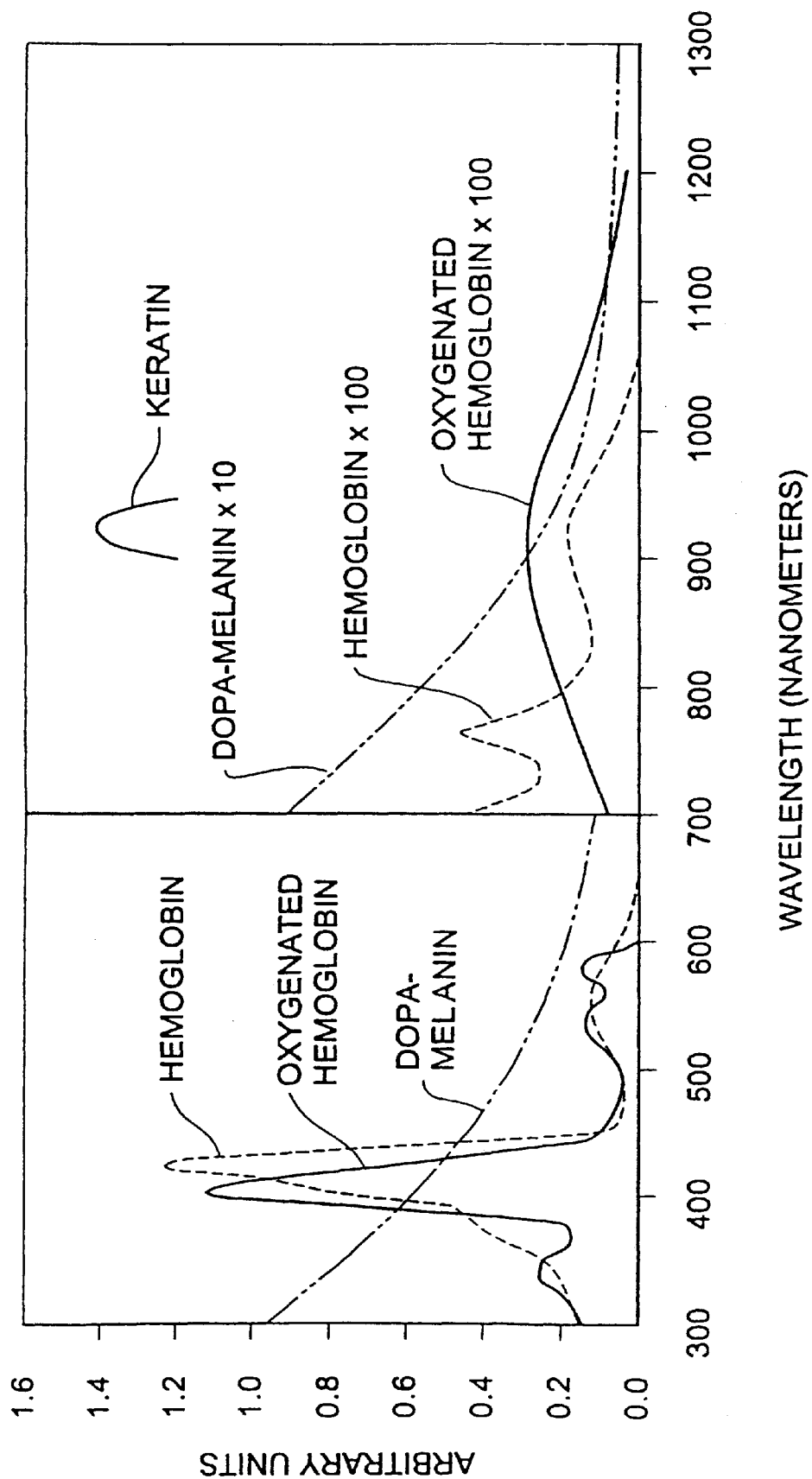
FIG. 2 is a graph showing the absorption spectrum of hemoglobin, melanin, and keratin in the visible and near infra-red light range.

FIG. 2 illustrates the relatively high absorption of light in the 880–950 nm wavelength range by the protein keratin. FIG. 2 also shows the relatively low absorption of light in the same range by the hemoglobin and melanin present in the tissue surrounding the hair. These absorption characteristics of keratin, hemoglobin, and melanin allow the transcutaneous use of light of the chosen wavelength to target the keratin in the hair shaft and subsequently destroy the papilla without damage to the surrounding tissue.

The preferred embodiment of the invention primarily utilizes laser light 18 having wavelength in the 900–950 nanometer range, optimally around 920 nm. As indicated in FIG. 2, light of this wavelength passes through the dermis 17 and the epidermis 16 with only minimal absorption by blood, blood components, and melanin. Although light in the 880–900 nm range is also well-absorbed by keratin, the increased absorption by melanin in this range, as compared to the absorption in the 900–950 nm range, absorption of the light in the 880–900 nm range by melanin could lead to skin damage in some individuals, particularly those with darker skin colors and lighter hair coloring. The 900–950 nm wavelength range is, however, absorbed by the protein keratin, which is the main component of hair of all colors. Absorption of the light energy by the keratin produces heat, which damages the hair shaft 10 and root 11. This heat may also photocoagulate the blood vessels 14 feeding the papilla 12, resulting in destruction of the hair 9 and increasing the probability of permanent removal.

Power level and duration of the laser pulse directed onto the skin must be carefully chosen to optimize the conduction of heat from the hair shaft and root to the papilla. As an example, a 0.2 second pulse from a laser delivering a power level of approximately 6 milliwatts per hair to the root would deliver sufficient energy to the hair shaft and root to result in significant damage to the papilla and a high probability of permanent hair removal. Use of a shorter, higher energy laser pulse will rapidly vaporize the hair, resulting in hair removal below the surface with little probability of permanent hair destruction. Pulses of less than 0.0001 seconds in duration having sufficient energy to damage hair can lead to very explosive, i.e., photoacoustic, absorption and to hyper- or hypo-pigmentation. Conversely, a pulse longer than 1.0 seconds can result in clinically-observable damage to the surrounding tissue and possible scarring. Prior art often limits the exposure time to periods less than the thermal relaxation predicted using the thermal and geometric parameters of the melanosomes, the melanin-bearing microstructures. Our target is the hair itself, which is much larger than these melanosomes, leading to a somewhat longer maximum exposure time, according to the same type of estimates used in the prior art. Our clinical observations are consistent with the safety of the 0.2–1.0 second exposure range.

Figure 3:
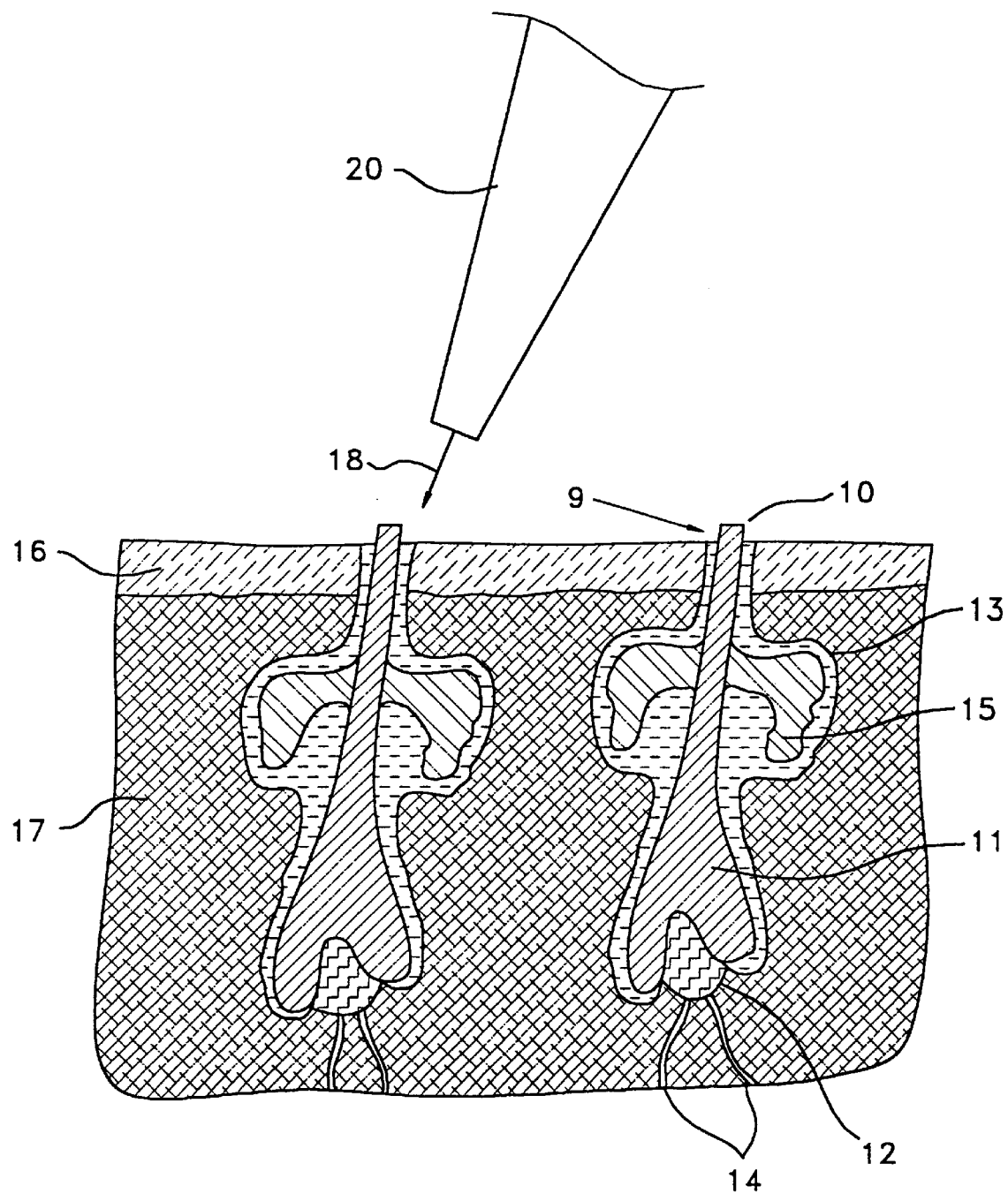
FIG. 3 is a sectional view of an area of skin showing the structure of hair and skin and the intrafollicular application of laser light.

Although highly effective on hairs having papillas at a skin depth of 1.0 cm or less, scattering and absorption of the laser light make the transcutaneous method less effective on the small percentage of hairs which exceed this limit. To effectively remove these hairs, the preferred embodiment of the invention further comprises the intrafollicular application of laser light 18 having a second wavelength, as shown in FIG. 3. This second wavelength is produced by known means, such as second harmonic generation or 3-mixing plus second harmonic generation, from the same laser source which generates the primary 900–950 nm wavelength. In the manner described in the prior art, the intrafollicular probe 20 is used to deliver laser light 18 of the second wavelength directly into the follicle 13 of a hair 9 having papilla 12 at a skin depth beyond the effective range of the transcutaneous method. This second wavelength of light, in the 450–475 nanometer range, is readily absorbed by either the melanin in the hair 9 or the hemoglobin in the blood vessels 14 surrounding the papilla 12, resulting in damage to the hair shaft 10, photocoagulation of the tissue surrounding the papilla, and subsequent destruction of the hair. In this fashion, a single, inexpensive, laser light source can be used to treat all types of hair in the least painful and most efficient, cost effective, and convenient manner possible.

Although the above description contains specificities pertaining to laser light wavelength, pulse duration, and power level, these specificities should not be construed as limitations on the scope of the invention, but rather as an exemplification of one preferred embodiment thereof. Variations in primary and secondary laser wavelength, pulse duration, and power level may be possible without significantly reducing the effectiveness of the method. The invention contemplates all variations in these, and all other laser parameters, which accomplish an equivalent result.

The embodiments of the invention in which an exclusive property or privilege is claimed are defined as follows:

1. A method for permanently removing hair from skin, the method comprising the steps of:

directing laser light onto an area of skin having hair extending from the skin, in which the laser light is characterized by having a wavelength greater than 900 and less tan 950 nanometers, and which laser light passes through the skin with minimal absorption and which is substantially absorbed by a component of hair, and applying the laser light to the area of skin until the hair is destroyed, while minimizing damage to tissue surrounding the hair.

2. The method of claim 1 in which the laser light is pulsed.

3. The method of claim 2 in which the laser light is pulsed with pulses having a duration of between 0.2 seconds and one second.

4. The method of claim 1 in which the laser light is at a wavelength selectively absorbed by keratin.

5. The method of claim 1 further comprising directing laser light onto the area of skin, in which the laser light is characterized by having a wavelength between 450 and 475 nanometers.

6. The method of claim 1 in which the laser light having a wavelength between 450 and 475 nanometers is produced by a laser, and the laser light having a wavelength between 900 and 950 nanometers is produced by the laser.

* * * * *

UNITED STATES PATENT AND TRADEMARK OFFICE
CERTIFICATE OF CORRECTION

PATENT NO.     : 6,544,255 B2                                         Page 1 of 1
DATED          : April 8, 2003
INVENTOR(S)    : B. W. Stewart It is certified that error appears in the above-identified patent and that said Letters Patent is hereby corrected as shown below:

Title page,
Item [56], References Cited, FOREIGN PATENT DOCUMENTS, insert
-- WO   PCT/US99/32193   7/1999 --

Column 4,
Line 47, "tan" should read -- than --

Signed and Sealed this

Sixteenth Day of September, 2003

JAMES E. ROGAN
*Director of the United States Patent and Trademark Office*